United States Patent [19]

Luber et al.

[11] Patent Number: 5,345,087
[45] Date of Patent: Sep. 6, 1994

[54] OPTICAL GUIDE SYSTEM FOR SPATIALLY POSITIONING A SURGICAL MICROSCOPE

[75] Inventors: Joachim Luber, Essingen-Forst; Werner Müller, Ötisheim; Martin Pelzer, Heidenheim; Anette Reiss, Heidenheim, all of Fed. Rep. of Germany

[73] Assignee: Carl-Zeiss-Stiftung, Heidenheim, Fed. Rep. of Germany

[21] Appl. No.: 11,515

[22] Filed: Feb. 1, 1993

[30] Foreign Application Priority Data

Jan. 30, 1992 [DE] Fed. Rep. of Germany ....... 4202505

[51] Int. Cl.5 .............................................. G01N 21/86
[52] U.S. Cl. .................................. 250/561; 250/203.2; 356/152.1
[58] Field of Search ................... 250/561, 203.2, 203.1, 250/206.1, 206.2; 356/141, 152, 400, 1, 4

[56] References Cited

U.S. PATENT DOCUMENTS

| 3,806,725 | 4/1974 | Leitz | 250/203.2 |
| 3,887,267 | 6/1975 | Heller | |
| 4,193,689 | 3/1980 | Reymond et al. | 356/152 |
| 4,453,085 | 6/1984 | Pryor | 250/203.1 |
| 4,578,575 | 3/1986 | Roos | 250/203.1 |
| 4,896,962 | 1/1990 | Menn et al. | 356/152 |
| 4,923,303 | 5/1990 | Lutz | 250/561 |
| 4,989,253 | 1/1991 | Liang et al. | |
| 5,059,789 | 10/1991 | Salcudean | 250/561 |

FOREIGN PATENT DOCUMENTS 239884 10/1986 Fed. Rep. of Germany.
4032207 4/1991 Fed. Rep. of Germany.

*Primary Examiner*—David C. Nelms
*Attorney, Agent, or Firm*—Walter Ottesen

[57] ABSTRACT

An instrument is mounted on a motorized positioning mechanism for providing a contactless guidance of the instrument. A transmitting unit and a receiving unit are arranged in a defined relative position to an operator and the instrument so that an evaluation unit positions the instrument via corresponding control signals with the aid of the registered signals of the receiving unit. A preferred application is the contactless guidance of a surgical microscope which tracks the head movements of the surgeon.

16 Claims, 4 Drawing Sheets

OPTICAL GUIDE SYSTEM FOR SPATIALLY POSITIONING A SURGICAL MICROSCOPE

BACKGROUND OF THE INVENTION

Various guide systems are known for spatially positioning an instrument. In medical technology, for example, the task is present for surgeons to position a surgical microscope in various spatial degrees of freedom with the surgical microscope being mounted on a support.

For this purpose, published German patent application 4,032,207 discloses mounting a surgical microscope on a motorized positioning multi-link mechanism. With the aid of this multi-link mechanism, it is possible for the surgeon operating the mechanism to position the surgical microscope in space as desired without exerting force. However, the positioning of the microscope takes place via a separate control unit wherein the desired spatial coordinates of the surgical microscope must be inputted manually. Accordingly, a defined positioning during surgery is most difficult with an arrangement of this kind because the surgery must be interrupted to manually input specific spatial coordinates.

Furthermore, it is known in medical technology to spatially position surgical microscopes, which are mounted on conventional supports, with the aid of mechanical means. For example, in U.S. Pat. No. 3,887,267, a mouthpiece is disclosed with which the surgeon guides the surgical microscope during the surgery. The rigid connection between the head of the surgeon and the surgical microscope as well as the necessary expenditure of effort to move the support make a positioning of this kind however likewise very difficult.

U.S. Pat. No. 4,989,253 discloses an arrangement for contactlessly guiding a surgical microscope wherein the surgical microscope is moved with the aid of a voice-activated guide system. With this arrangement, significant disadvantages of the above-described guidance and positioning systems are avoided; however, difficulties result with respect to the precise determination of the particular travel path by the surgeon. The matching of the reaction times of the voice-sensitive positioning system to the corresponding voice signals is complex or possible only with difficulty.

SUMMARY OF THE INVENTION

It is an object of the invention to provide a guide system for spatially positioning an instrument wherein a contactless positioning in up to six spatial degrees of freedom is possible with high precision.

The invention is directed to a guide system for spatially positioning an instrument in correspondence to movements of an operator. The guide system includes: motorized positioning support means for holding and moving the instrument in a predetermined number of degrees of freedom; transmitter means mounted on one of the operator and the instrument in a defined position relative thereto for transmitting a transmitter output; receiver means mounted on the other one of the operator and the instrument in a defined position relative thereto for receiving the transmitter output and for emitting output signals indicative of a relative movement between the transmitter means and the receiver means; and, evaluation means for evaluating the output signals of the receiver means to reconstruct the movement of the operator and form control signals indicative of the movement and for transmitting the control signals to the motorized positioning support means thereby enabling the instrument to track the movement of the operator.

What is essential here is that the guide system makes a contactless spatial guidance and positioning of the particular instrument possible with high precision. The guide system of the invention can, for example, be utilized in medical technology in order to cause a surgical microscope to follow the head movements of the surgeon in up to six spatial degrees of freedom. The surgical microscope is preferably mounted on a suitable motorized support or mounted on a conventional support by means of a motorized suspension so that at least a limited motorized positioning or tracking is possible.

In one possible optically-based embodiment, an optical transmitting unit or receiving unit is mounted on the head of the surgeon and preferably the forehead of the surgeon. The surgical microscope is mounted on the motorized positioning mechanism and has the corresponding counter element, that is, an optical receiving or transmitting unit. The preferred arrangement of the optical transmitting and receiving unit is so configured that the radiation of the transmitting unit impinges the receiving unit in conventional operation. For example, the optical receiving or transmitting unit is mounted above the oculars of the surgical microscope where it is located approximately opposite the optical transmitting or receiving unit arranged on the forehead of the surgeon.

The optical transmitting unit preferably comprises one or more light sources such as conventional LEDs, laser diodes or conventional light sources having diaphragms or suitable collimating optics mounted forward thereof so that one or more transmitting beam paths result.

In a further embodiment, it is possible to arrange the light sources independently of the operator or independently of the instrument and to supply the transmitting unit via light conductors. The light sources of the optical transmitting units can operate in different spectral ranges. At least two separate transmitting beam paths are required to detect six possible degrees of freedom. These transmitting beam paths can be generated in different ways by means of the light sources of the optical transmitting unit.

The optical receiving unit includes at least one position-sensitive detector which is configured for the wavelength of the particular transmitting unit. For this purpose, either spatially separate position-sensitive detectors such as lateral effect diodes, transparent lateral effect diodes or segmented photo diodes can be used. However, the use of a single surface detector such as a two-dimensional CCD-array is also possible which can provide a position-resolving registration of several simultaneously impinging beam paths. The particular detector must be able to spatially resolve three incident points in order to detect six different degrees of freedom.

A different number of separate transmitting beam paths or incident points, which are to be resolved on one or more detectors, can be required depending upon in how many degrees of freedom a particular instrument is to be positioned or which light sources or position-resolving detectors are selected. Accordingly, specific applications only require the free positionability or the guidance along a defined axis so that fewer than two separate transmitting beam paths or one detector arrangement are, for example, adequate with this detector arrangement being able to separately resolve fewer than three incident points.

However, at least two separate transmitting beam paths as well as one position-sensitive detector arrangement are provided for guiding or positioning in all possible six degrees of freedom. The position-sensitive detector arrangement can resolve at least three separate incident points.

A preferred arrangement for detecting six possible degrees of freedom includes two separate transmitting beam paths as well as three separate position-sensitive lateral effect diodes of which at least one is transparent for the light wavelength utilized. The two separate transmitting beam paths can, for example, be generated by two separate light sources. Of these three lateral effect diodes, two are spaced one behind the other in two parallel planes so that a first transmitting beam path leads to both of these lateral effect diodes; whereas, the second transmitting beam path leads to a third lateral effect diode.

Three separate transmitting beam paths are required for the exclusive use of non-transparent position-sensitive detectors for detecting six possible degrees of freedom. Furthermore, a position-resolving registration of three incident points must be possible with the particular detector arrangement. For this purpose, the detector arrangement comprises at least one surface CCD-arrangement in one or more planes or three separate position-sensitive detectors in one plane. However, it is also possible to arrange the three separate position-sensitive detectors in two or three different planes relative to each other.

It is also possible to arrange the optical transmitting unit and receiving unit together either on the head of the operator or on the particular instrument. Reflector elements are arranged on the opposite-lying end and these reflector elements reflect the impinging transmitted beams back in the direction of the optical receiving unit. The receiving unit can then, for example, be arranged in the same plane as the optical transmitting unit.

A further possibility for sequential resolution of the transmitting beams is provided by the use of a time-multiplex process. Here, the transmitting unit and the impinged position-sensitive detectors are synchronized with each other in such a manner that emitted transmitting beam paths are registered only by specifically assigned individual detectors at different times. For this purpose, devices for signal transmission between evaluation unit and optical receiving unit and optical transmitting unit are necessary. The number of required detectors can be advantageously reduced with the aid of a time-multiplex arrangement of this kind.

In addition, many other possibilities exist to arrange individual position-sensitive detectors relative to each other as well as relative to the optical transmitting unit.

An evaluation unit is necessary for the guidance system of the invention. The evaluation unit processes the signals registered by the individual position-sensitive detectors in such a manner that a relationship between the movement of the head and the position of the registered signals associated therewith on the detectors of the optical receiving unit can be established. The surgical microscope tracks via the motorized positioning mechanism in correspondence to the registered movement of the head and thereby "follows" the head movements of the surgeon. For this purpose, appropriate signals from the evaluation unit are transmitted to the particular positioning mechanism.

In addition to positioning the surgical microscope spatially, it is also possible to carry out a focusing with the aid of the guidance system of the invention. This presupposes that this takes place by means of a change of distance between the surgical microscope and the viewing plane along the optical axis by means of the positioning mechanism.

A contactless guidance of an instrument in space is therefore possible with the aid of the guidance system of the invention without there being a necessity of accepting limitations introduced by mechanical connections between the operator and the particular instrument. Furthermore, a guidance in up to six degrees of freedom is possible without there being a necessity for interrupting manipulative sequences. The guidance system of the invention is especially suited for contactless operation of a surgical microscope during surgery whereby a reduction of the duration of surgery results. However, a contactless positioning of endoscopes or other surgical apparatus of medical technology is also possible with the guidance system of the invention.

In addition, a multiplicity of other application possibilities exist wherein an instrument must be positioned spatially without there being a necessity to interrupt specific manipulative sequences. The guidance system of the invention is in no way limited to the described embodiments having an optical basis. Accordingly, ultrasonic transmitting and receiving units or magnetic transmitting and receiving units can be utilized. Also, the use of acceleration sensors within the transmitting unit is possible with the signals thereof being registered by a corresponding receiving unit.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
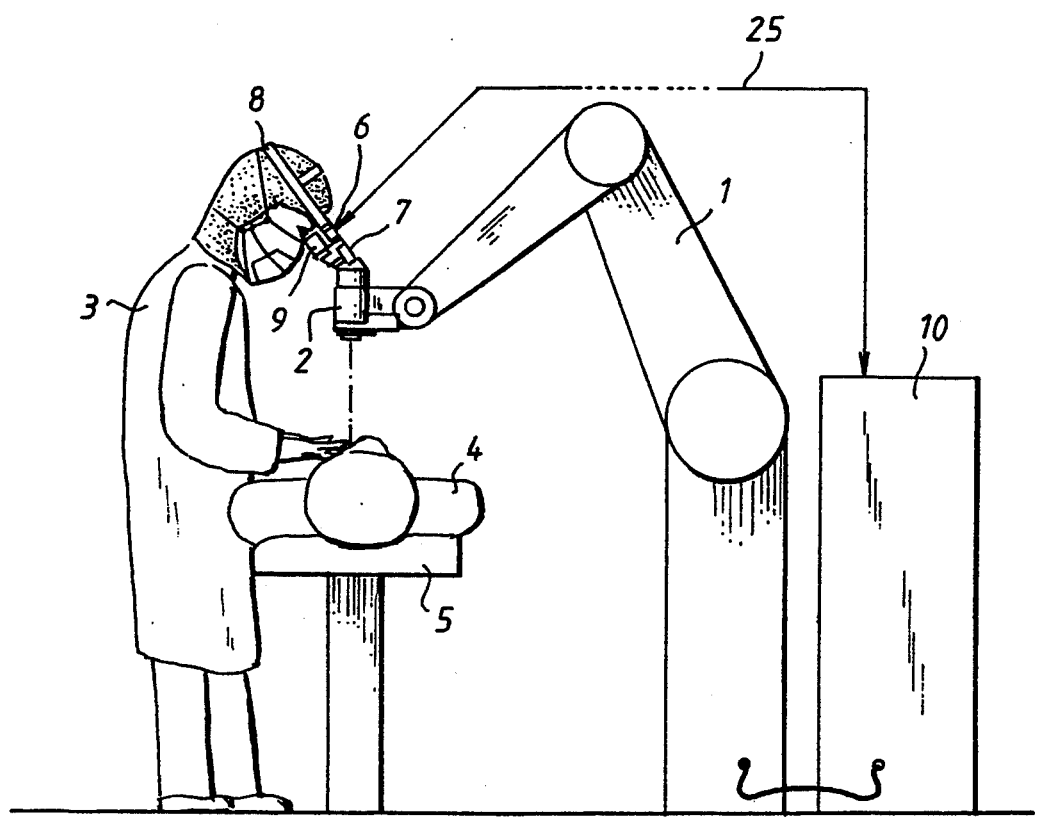
FIG. 1 is a schematic showing the use of the guidance system of the invention in combination with a surgical microscope.

FIG. 1 shows a possible application of the guidance system of the invention. A surgical microscope 2 is mounted on a motorized positioning support 1 which functions as a motorized positioning mechanism. The surgeon 3 performs the operation on the particular patient 4 with the aid of the surgical microscope 2 with the patient 4 lying on the operating table 5. The guidance system of the invention for the surgical microscope 2 includes an optical transmitting unit 6 which, in this embodiment, is held on the forehead of the surgeon 3. The transmitting unit 6 can, for example, be held with the aid of a suitable headband 8. The optical transmitting unit 6 then comprises at least one light source and supplies one or several transmitting beam paths. Commercially available luminescent diodes (LEDs) or conventional light sources with diaphragms or even laser diodes can be used as light sources. However, it is also possible to split up an individual light source with the aid of several light conductors and thereby simulate several individual light sources or transmitting beam paths.

An optical receiving unit 7 is required for operating the guidance system of the invention. The optical receiving unit 7 is mounted opposite the optical transmitting unit 6 directly on the surgical microscope 2. The arrangement of the optical receiving unit 7 above the binocular tubes 9 of the surgical microscope 2 is here advantageous. The surgeon 3 views the operating area through the binocular tubes 9.

As an alternate embodiment, it is possible at any time to exchange the arrangement of the optical transmitting unit 6 and receiving unit 7. The optical receiving unit 7 comprises essentially one or more position-sensitive detectors which are matched to the emitted wavelength of the optical transmitting unit 6 and can resolve one or several incident points in dependence upon position. The number of the necessary transmitting beam paths as well as the incident points to be resolved is then dependent upon the degrees of freedom in which a guidance or positioning of the particular instrument is to take place. The following can, for example, be utilized as position-sensitive detectors: lateral effect diodes, transparent lateral effect diodes, segmented photo diodes or even conventionally separate CCD-arrangements. Even surface CCD-arrangements can be used as position-sensitive detectors in addition to separate individual detectors. The surface CCD-arrangements make possible a position-resolving registration of several points, which are impinged simultaneously.

Figure 2A:
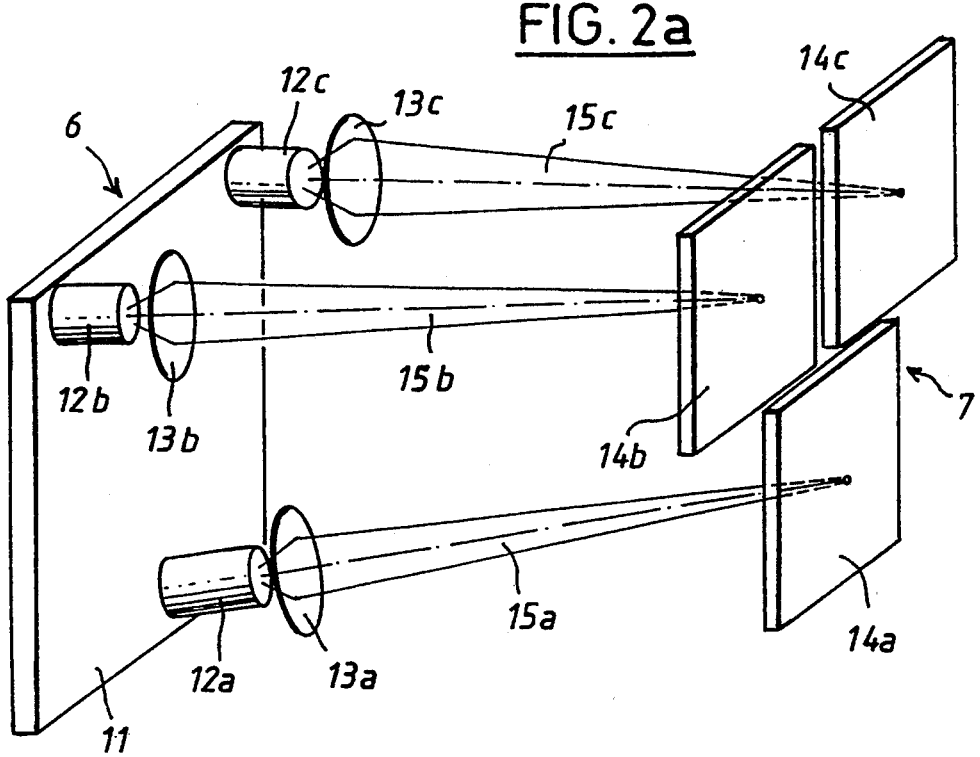
FIG. 2a shows a first possible arrangement of the optical transmitting and receiving units.
Figure 2B:
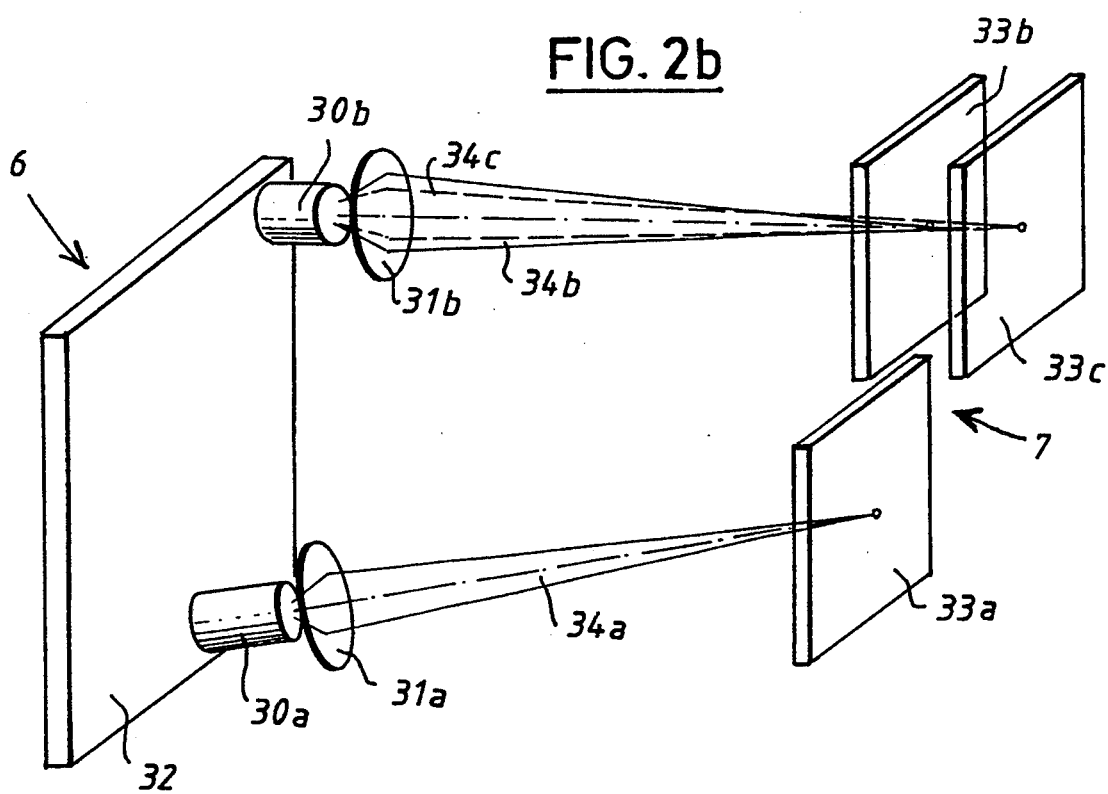
FIG. 2b shows a second possible arrangement of the optical transmitting and receiving units.
Figure 2C:
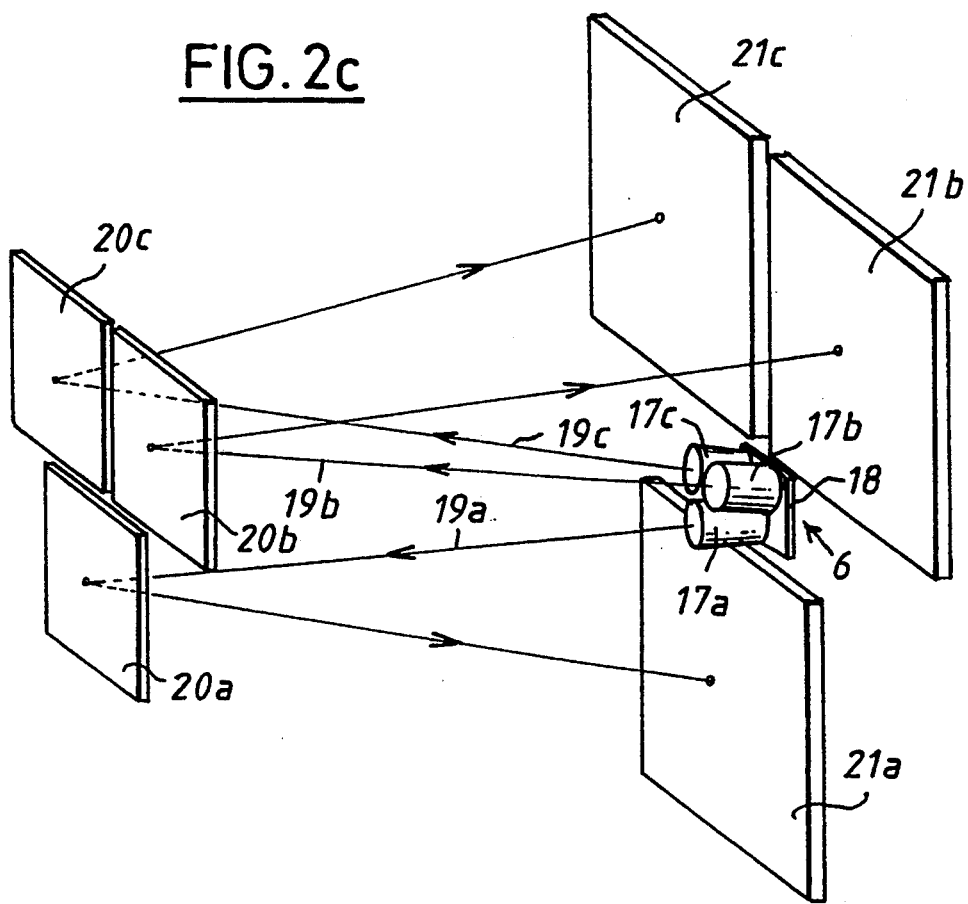
FIG. 2c shows a third possible arrangement of the optical transmitting and receiving units; and, FIG. 3 is a block circuit diagram having the most important required individual components of the guidance system of the invention.

A more detailed explanation as to possible relative arrangements of optical transmitting units 6 and receiving units 7 will be provided with respect to FIGS. 2a to 2c.

An evaluation unit 10 is furthermore necessary for operating the guidance system of the invention. The evaluation unit 2 reconstructs the movement of the head based on the signals registered on the optical receiving unit 7. If this relationship is determined via numerical evaluation processes, then the evaluation unit 10 transmits corresponding control signals to the motorized support 1 which is positionable in up to six degrees of freedom and which moves the surgical microscope 2 in such a manner that it precisely tracks the head movements of the surgeon 3.

The evaluation unit 10 can furthermore be utilized for controlling the optical transmitting unit 6. A corresponding signal transmission 25 is then required which is preferably contactless. The control or signal processing can also take place in such a manner that the optical transmitting unit and/or the evaluation unit associated therewith is controlled via a signal transmission of this kind. This presupposes a specific operating mode of the optical transmitting unit.

For operating the guide system of the invention, it is necessary to fix a defined normal position of the head 8 relative to the instrument such as a surgical microscope 2 during a one-time docking phase. This normal position is preferably so defined in the embodiment shown that the exit pupils of the surgical microscope 2 are coincident with the entry pupils of the surgeon 3. The surgical microscope 2 is moved or tracks movements of the head 8 in this defined normal position. A description of possible arrangements of the individual components of the optical transmitting and receiving units is provided with respect to FIGS. 2a to 2c in the following. In this context, it is once again noted that in addition to the relative arrangements described below, a plurality of further possible arrangements are available with which the guide system of the invention can be realized. It is especially always possible to selectively mount transmitting or receiving units on the head of the operator or on the particular instrument.

Figure 4A:
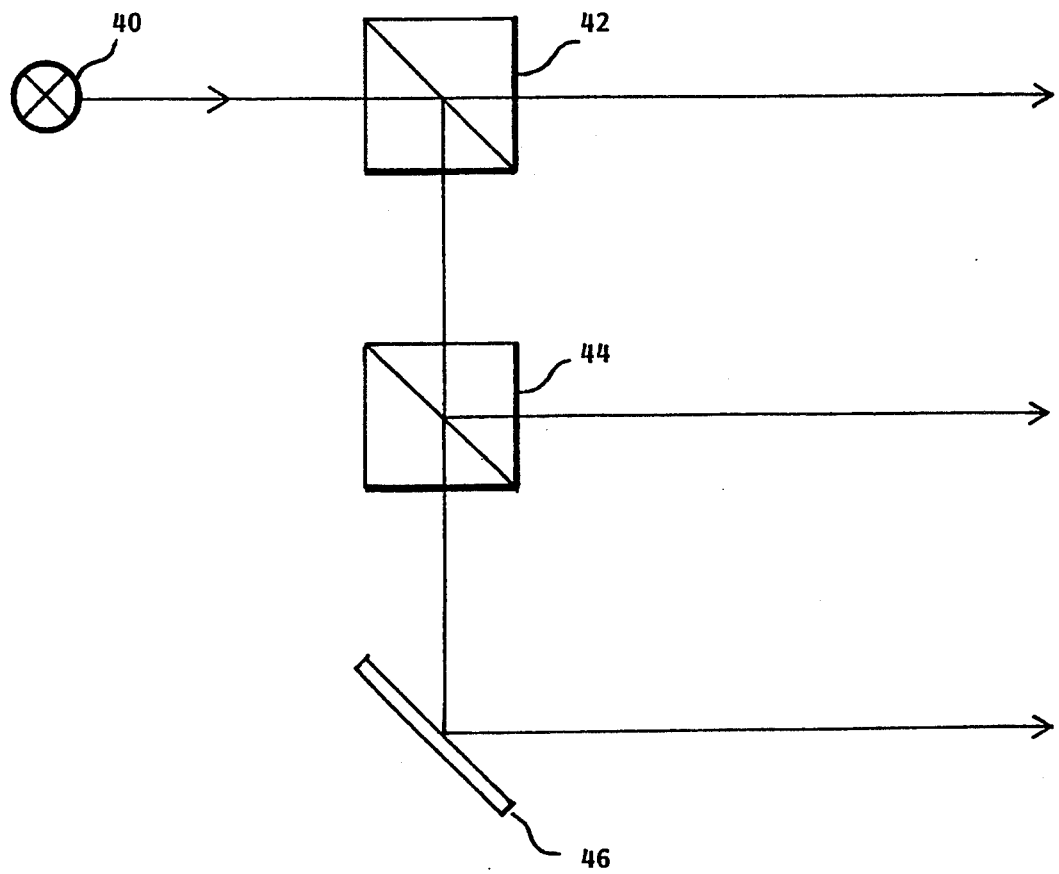
FIG. 4a is a schematic showing an individual light source generating an output beam which is divided into three component beams with the aid of two beam-splitter elements; and, FIG. 4b is a schematic showing an individual light source generating an output beam which is divided into three component beams with the aid of a fiber optic wave conductor.
Figure 4B:
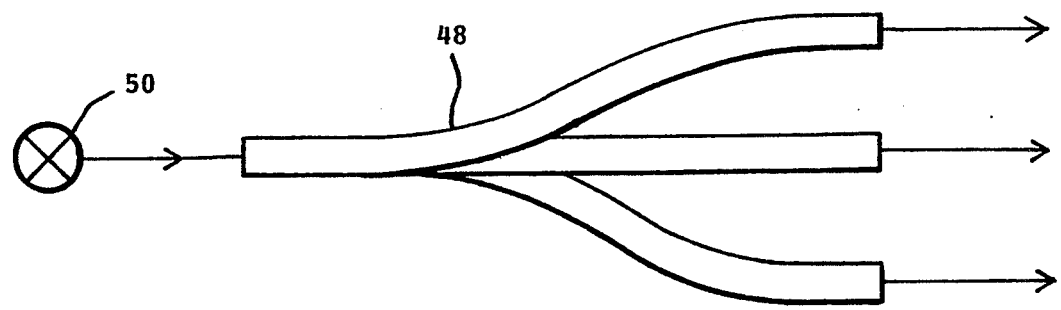

In the arrangement shown in FIG. 2a, the optical transmitting unit 6 comprises a base plate 11 on which three separate light sources (12a, 12b, 12c) are arranged having respective collimating optics (13a, 13b, 13c) mounted forward thereof. These light sources provide three separate transmitting beam paths. Laser diodes are here used as light sources (12a, 12b, 12c). Single or multi-lens optical systems function for imaging or collimation and are matched with respect to focal length approximately to the distance to the opposite-lying optical receiving unit 7. The arrangement of pin-hole diaphragms forward of the laser diodes or even the use of light conductors mounted forward of the laser diodes As shown in FIG. 4a, an individual light source 40 can be used in combination with optical beam splitter elements (42, 44) and a deflecting mirror 45 in order to thereby generate different separate transmitting beam paths. In FIG. 4b, a light wave conductor in the form of fiber optic light wave conductor 48 is used to divide a light beam of light source 50 into three component beams.

The optical receiving unit 7 is formed in the illustrated embodiment by three separate position-sensitive detectors (14a, 14b, 14c) which are matched to the emitted wavelengths of the optical transmitting unit 6. Surface lateral effect diodes are here suitable as position-sensitive detectors (14a, 14b, 14c). These detectors make possible a position-resolving registration of the corresponding beams (15a, 15b, 15c) or transmitting beam paths. Such detectors are available in the marketplace from, for example, the Heimann Company of Germany under the product designation AP 10-01. The three separate position-sensitive detectors (14a, 14b, 14c) are arranged in a plane in this embodiment.

As an alternate embodiment, the use of a single CCD-array is possible which likewise makes possible the position-resolving registration of three separate transmission beam paths. With the aid of the excursions of the impinging beams (15a, 15b, 15c) from defined desired incident points, it is possible via a corresponding numerical evaluation algorithm to detect the movement of the head of the operator. The desired incident points are fixed by a defined relative position of the head to the particular instrument and the excursions are registered by the position-sensitive detectors. An evaluation unit (not shown in the drawing) performs the detection of the shifted beams. The evaluation unit emits control signals to the motorized positioning mechanism after carrying out the evaluating algorithm. The positioning mechanism can then again be moved into the position in which the desired incident points are impinged in the optical receiving unit 7.

The determination of these desired incident points takes place, as mentioned, in a so-called docking phase in advance of the start of the actual operation or use. The desired incident points are defined relative positions of the head to the optical viewing unit. The desired incident points defined in this way are registered by the evaluation unit and are stored as desired values for the following method sequence. With the aid of the relative arrangement shown, it is possible to detect all six possible degrees of freedom of the movement of the head. Arrangements with fewer individual transmitting beam paths or fewer position-sensitive detectors permit sometimes only the detection of a reduced number of degrees of freedom for the movement of the head.

By using three transmitting beam paths and three separate position-sensitive detectors, it is alternatively possible to arrange the three detectors in different planes relative to each other. For example, two position-sensitive detectors can be arranged in one plane and the third position-sensitive detector can be orientated perpendicularly thereto for the registration of the third transmitting beam path.

In addition, the possibility is provided that the beams transmitted by the light sources can all run parallelly or even diverge or converge relative to each other.

A second arrangement possibility for optical transmitting and receiving units is described with respect to FIG. 2b. Here, the optical transmitting unit 6 comprises two separate light sources (30a, 30b) with a suitable collimating optics (31a, 31b). The light sources (30a, 30b) are again arranged on a base plate 32 and laser diodes again serve as light sources (30a, 30b). As already mentioned, the generation of two separate transmitting beams is possible even with a single light source. The single light source is split via suitable beam splitter elements or light wave conductors into several transmitting beams. In the optical receiving unit 7, three separate position-sensitive detectors (33a, 33b, 33c) are provided of which at least one is configured as a transparent lateral effect diode 33b and is transmittent for the light wavelength used. Transparent lateral effect diodes of this kind are commercially available from the Heimann Company of Germany under the product designation of AP 10-02. Here, two of the position-sensitive detectors (33b, 33c) are arranged in parallel planes spaced one behind the other, that is, a transmitting beam path (34b, 34c) impinges the two position-sensitive detectors since the forward position-sensitive detector 33b is transparent. The third position-sensitive detector 33a is arranged in a further plane. Two of the position-sensitive detectors (33a, 33c) must not be transparent in this arrangement; that is, all previously-mentioned position-sensitive detectors can be used. As in the first embodiment of FIG. 2a, an evaluation unit (not shown) takes over the processing of the registered signals and the control of the positioning mechanism.

FIG. 2c shows a further arrangement for detecting six possible degrees of freedom for the movement of the head. The optical transmitting unit 6 again comprises three separate light sources (17a, 17b, 17c) arranged on a base plate 18. The light beams (19a, 19b, 19c) transmitted by the three light sources (17a, 17b, 17c) or the transmitting beam paths impinge on three reflector elements (20a, 20b, 20c) which are mounted either on the particular instrument or on the head of the operator. A reflection of the transmitted light beam takes place in the direction of the optical transmitting unit 6. Three separate position-sensitive detectors (21a, 21b, 21c) are arranged in the same plane as the optical transmitting unit 6. The detectors register a movement of the reflector elements (20a, 20b, 20c) relative to the optical receiving or transmitting units, that is, a shift of the reflected transmitting beam paths from the defined desired incident points as described above. Here too, the reflector elements can, on the one hand, be selectively mounted either on the head of the operator or on the particular instrument while the transmitting and receiving unit can be mounted on the head of the operator and vice versa.

As already mentioned, a great many further arrangements between optical transmitting and receiving units exist which are in addition to the embodiments shown in FIGS. 2a to 2c. These arrangements likewise permit the operation of the guidance system of the invention.

Figure 3:
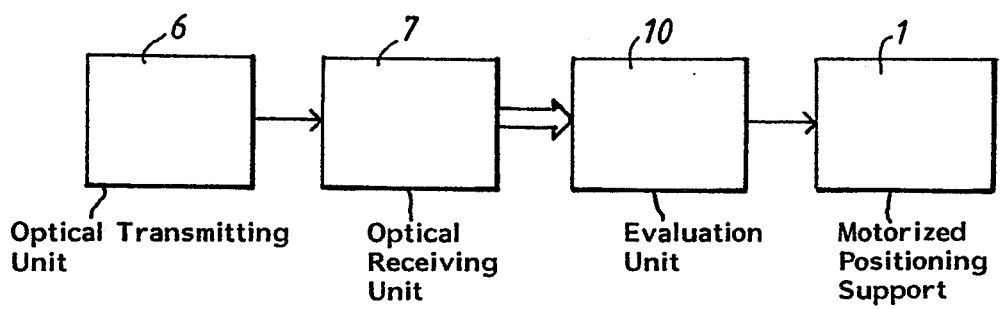

The signal processing in the context of the guidance system of the invention is again explained with respect to FIG. 3. The signals emitted by the transmitting unit 6 are registered by the receiving unit 7 mounted in a defined relative geometry with respect to the instrument and operator. The receiving unit 7 is connected to an evaluation unit 10 which determines the relative movement between transmitter and receiver unit or between the instrument and the operator on the basis of the registered signals and via a numerical evaluating algorithm. Deviations of the relative position to a previously defined desired relative position are tracked via corresponding control signals to the motorized position mechanism 1 until the original desired relative position is established again.

It is understood that the foregoing description is that of the preferred embodiments of the invention and that various changes and modifications may be made thereto without departing from the spirit and scope of the invention as defined in the appended claims.

What is claimed is:

1. A guide system for spatially positioning a surgical microscope in correspondence to movements of the head of an operator for which a desired position relative to the surgical microscope is defined, the guide system comprising:

motorized positioning support means for holding and moving the surgical microscope in six degrees of freedom;

transmitter means mounted on one of the head of said operator and said surgical microscope in a defined position relative thereto for transmitting at least two separate transmitting beams defining respective beam paths;

receiver means mounted on the other one of the head of said operator and said surgical microscope in a defined position relative thereto for receiving said transmitting beams;

said receiver means including means providing a position-resolving registration of at least three separate incident points and means for emitting output signals indicative of a relative movement between said transmitter mean and said receiver means in said six degrees of freedom; and, evaluation means for evaluating said output signals of said receiver means to reconstruct the movement of the head of said operator in said six degrees of freedom relative to said defined desired position and form control signals indicative of said movement and for transmitting said control signals to said motorized positioning support means thereby actuating said support means to cause said surgical microscope to track the movement of the head of said operator into said defined desired position in six degrees of freedom.

2. A guide system for spatially positioning a surgical microscope in correspondence to movements of the head of an operator for which a desired position relative to the surgical microscope is defined, the guide system comprising:

motorized positioning support means for holding and moving the surgical microscope in six degrees of freedom;

optical transmitter means mounted on one of the head of said operator and said surgical microscope in a defined position relative thereto;

said optical transmitter means including at least one light source for generating and transmitting at least two separate transmitting beam defining respective beam paths;

optical receiver means mounted on the other one of the head of said operator and said surgical microscope in a defined position relative thereto for receiving said transmitting beams;

said optical receiver means including means providing a position-resolving registration of at least three separate incident points and means for emitting output signals indicative of a relative movement between said optical transmitter means and said optical receiver means in said six degrees of freedom; and, evaluation means for evaluating said output signals to reconstruct a movement of the head of said operator in said six degrees of freedom relative to said defined desired position and form control signals indicative of said movement and for transmitting said control signals to said motorized positioning support means thereby actuating said support means to cause said surgical microscope to track the movement of the head of said operator into said defined desired position in six degrees of freedom.

3. The guide system of claim 2, said optical transmitter means further including a plurality of optical elements for dividing said beam into a plurality of beams defining a plurality of respective individual transmitting beam paths.

4. The guide system of claim 3, said elements being beam-splitter elements.

5. The guide system of claim 3, said elements being light wave conductors.

6. The guide system of claim 2, said optical transmitter means including means for focussing said beams transmitted along said transmitting beam paths, respectively.

7. The guide system of claim 2, said optical transmitter means further including three optical elements for dividing said beam into three beams defining three respective individual transmitting beam paths; and, said optical receiver means including a plurality of position-sensitive detectors for providing a position-resolving registration of said three transmitting beam paths.

8. The guide system of claim 2, said position-sensitive detector being defined by at least one CCD-array.

9. The guide system of claim 2, said optical receiver means including a plurality of said position-sensitive detectors;

and, each of said position-sensitive detectors being a segmented photo diode.

10. The guide system of claim 2, said optical receiver means including a plurality of said position-sensitive detectors;

and, each of said position-sensitive detectors being a lateral effect diode.

11. The guide system of claim 2, said optical receiver means including a plurality of said position-sensitive detectors;

and, each of said position-sensitive detectors being a transparent lateral effect diode.

12. A guide system for spatially positioning a surgical microscope in correspondence to movements of the head of an operator for which a desired position relative to the surgical microscope is defined, the guide system comprising:

motorized positioning support means for holding and moving the surgical microscope in six degrees of freedom;

optical transmitter means mounted on one of the head of said operator and said surgical microscope in a defined position relative thereto;

said optical transmitter means including at least one light source for generating and transmitting at least two separate transmitting beams defining respective beam paths;

optical receiver means mounted on the other one of the head of said operator and said surgical microscope in a defined position relative thereto for receiving said transmitting beams;

said optical receiver means including means providing a position-resolving registration of at least three separate incident points and means for emitting output signals indicative of a relative movement between said optical transmitter means and said optical receiver means in said six degrees of freedom;

evaluation means for evaluating said output signals to reconstruct a movement of the head of said operator in said six degrees of freedom relative to said defined desired position and form control signals indicative of said movement and for transmitting said control signals to said motorized positioning support means thereby actuating said support means to cause said surgical microscope to track the movement of the head of said operator into said defined desired position in six degrees of freedom;

said light source being adapted to generate and transmit first and second light beams defining first and second beam paths, respectively; and, said optical receiver means including three position-sensitive detectors; a first one of said position-sensitive detectors being a transparent lateral effect diode mounted in a first plane so as to be first impinged by said first light beam; a second one of said position-sensitive detectors being disposed in a second plane rearward of said first position-sensitive detector; and, the third one of said position-sensitive detectors being disposed in a third plane.

13. The guide system of claim 2, said optical transmitter means being mounted on one of said instrument and the head of said operator.

14. The guide system of claim 13, said optical receiver means being mounted on the other one of said instrument and said head of said operator.

15. The guide system of claim 2, further comprising transmission means for transmitting signals between said evaluation means and said optical transmitter means and said optical receiver means;

and, said transmission means being adapted to provide a sequential resolution of said beam defining said beam path.

16. A guide system for spatially positioning a surgical microscope in correspondence to movements of the head of an operator for which a desired position relative to the surgical microscope is defined, the guide system comprising:

motorized positioning support means for holding and moving the surgical microscope in six degrees of freedom;

optical transmitter means including at least one light source for generating and transmitting at least two separate transmitting beams defining respective beam paths;

said optical receiver means including means providing a position-resolving registration of at least three separate incident points and means for emitting output signals indicative of a relative movement between said optical transmitter means and said optical receiver means in said six degrees of freedom;

said optical transmitter means and said optical receiver means both being mounted on one of the head of said operator and said surgical microscope in a defined position relative thereto;

reflector means for receiving said beam from said optical transmitter means and for reflecting said beam to said optical receiver means;

said reflector means being mounted on the other one of the head of said operator and said surgical microscope in a defined position relative thereto; and, evaluation means for evaluating said output signals to reconstruct a movement of the head of said operator in said six degrees of freedom relative to said defined desired position and form control signals indicative of said movement and for transmitting said control signals to said motorized positioning support means thereby actuating said support means to cause said surgical microscope to track the movement of the head of said operator into said defined desired position in said six degrees of freedom.

* * * * *

UNITED STATES PATENT AND TRADEMARK OFFICE
CERTIFICATE OF CORRECTION

PATENT NO. : 5,345,087

DATED : September 6, 1994

INVENTOR(S) : Joachim Luber, Werner Müller, Martin Pelzer and Annette Reiss

It is certified that error appears in the above-identified patent and that said Letters Patent is hereby corrected as shown below:

In column 1, line 33: delete "however".

In column 4, line 45: delete "and," (second occurrence).

In column 6, between lines 29 and 30: insert -- are possible for collimation. --.

In column 6, line 32: delete "mirror 45" and substitute -- mirror 46 -- therefor.

In column 7, line 67: delete "the-optical" and substitute -- the optical -- therefor.

In column 8, line 59: delete "mean" and substitute -- means -- therefor.

In column 9 line 18: delete "beam" and substitute -- beams --.

Signed and Sealed this

Twenty-fifth Day of October, 1994

Attest:

BRUCE LEHMAN

Attesting Officer     Commissioner of Patents and Trademarks